(12) United States Patent
Tsubata et al.

(10) Patent No.: US 8,682,420 B2
(45) Date of Patent: Mar. 25, 2014

(54) HEARTBEAT MEASURING DEVICE AND HEARTBEAT MEASURING METHOD

(71) Applicant: Seiko Instruments Inc., Chiba (JP)

(72) Inventors: Keisuke Tsubata, Chiba (JP); Takanori Hasegawa, Chiba (JP); Akira Takakura, Chiba (JP); Katsuya Mugishima, Chiba (JP); Kazuo Kato, Chiba (JP); Kazuhiro Koyama, Chiba (JP); Hisao Nakamura, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 13/676,391

(22) Filed: Nov. 14, 2012

(65) Prior Publication Data

US 2013/0138007 A1    May 30, 2013

(30) Foreign Application Priority Data

Nov. 24, 2011  (JP) .................................. 2011-256278
Oct. 2, 2012   (JP) .................................. 2012-220390

(51) Int. Cl.
*A61B 5/04*     (2006.01)

(52) U.S. Cl.
USPC ....................................................... 600/509

(58) Field of Classification Search
USPC ....................................................... 600/509
See application file for complete search history.

(56) References Cited

U.S. PATENT DOCUMENTS

| 6,149,602 A * | 11/2000 | Arcelus .......................... 600/523 |
| 7,797,038 B2 * | 9/2010 | Hui et al. ....................... 600/519 |
| 2008/0319281 A1 * | 12/2008 | Aarts ............................. 600/301 |

FOREIGN PATENT DOCUMENTS

JP            03159634          7/1991

* cited by examiner

*Primary Examiner* — George Manuel
(74) *Attorney, Agent, or Firm* — Adams & Wilks

(57) ABSTRACT

A heartbeat measuring device has a measurement unit that measures a heart rate of a user, and an information storage unit that stores unique information regarding a heart rate unique to the user or information regarding a detected heartbeat of the user. A determination unit determines whether or not a heartbeat measurement state of the user is normal on the basis of the unique information or the information regarding a heartbeat stored in the information storage unit. An abnormality detection unit detects an abnormality corresponding to poor mounting of the heartbeat measuring device or interference due to external noise on the basis of a heart rate measured by the measurement unit. A notification unit performs a notification when the abnormality is detected by the abnormality detection unit. The notification unit changes information to be notified on the basis of a detection result by the abnormality detection unit.

14 Claims, 15 Drawing Sheets

FIG. 4A

EXAMPLE OF SETTING ±25% OF CURRENT HEART RATE AS UPPER AND LOWER LIMITS

| CURRENT HEART RATE (bpm) | RATIO (%) | UPPER LIMIT (bpm) | LOWER LIMIT (bpm) |
|---|---|---|---|
| 80 | 25 | 100 | 60 |
| 90 | 25 | 113 | 68 |
| 100 | 25 | 125 | 75 |
| 110 | 25 | 138 | 83 |
| 120 | 25 | 150 | 90 |
| 130 | 25 | 163 | 98 |
| 140 | 25 | 175 | 105 |
| 150 | 25 | 188 | 113 |
| 160 | 25 | 200 | 120 |
| 170 | 25 | 213 | 128 |
| 180 | 25 | 225 | 135 |

FIG. 4B

IN CASE OF SETTING UPPER LIMIT AND LOWER LIMIT THRESHOLD VALUES ACCORDING TO FOLLOWING EXPRESSIONS

UPPER LIMIT: (CURRENT HEART RATE+MAXIMAL HEART RATE)/2
LOWER LIMIT: (CURRENT HEART RATE+STABLE HEART RATE)/2

HERE, STABLE HEART RATE 60 bpm
MAXIMAL HEART RATE 180 bpm

| CURRENT HEART RATE (bpm) | UPPER LIMIT (bpm) | LOWER LIMIT (bpm) |
|---|---|---|
| 80 | 130 | 70 |
| 90 | 135 | 75 |
| 100 | 140 | 80 |
| 110 | 145 | 85 |
| 120 | 150 | 90 |
| 130 | 155 | 95 |
| 140 | 160 | 100 |
| 150 | 165 | 105 |
| 160 | 170 | 110 |
| 170 | 175 | 115 |
| 180 | 180 | 120 |

HEARTBEAT MEASURING DEVICE AND HEARTBEAT MEASURING METHOD

BACKGROUND OF THE INVENTION

1. Field of the Invention

The present invention, relates to a technique of measuring a heart rate of a user.

2. Background Art

There is a heartbeat measuring device which is mounted on the exercising user's body and measures a heart rate of the user (for example, JP-A-3-159634). The heartbeat measuring device detects an electrocardiogram signal occurring due to the heartbeat of the user and calculates a heart rate according to the pulse interval of the electrocardiogram signal. Here, there are cases where an incorrect electrocardiogram signal is detected depending on a degree of adhesion between the heartbeat we as urine device and the skin of the user or the like. For example, in a case where a signal which is not an electrocardiogram signal is detected as the electrocardiogram signal, a pulse interval decreases, and thus an abnormally high heart rate is calculated. Alternatively, in a case where detection of an electrocardiogram signal is omitted, a pulse interval increases, and thus an abnormally low heart rate is calculated. It can be said that the heart rate calculated in this way is an abnormal value and is an invalid heart rate. Therefore, a threshold value of a heart rate for determining whether or not a heart rate is a normal value may be stored in a heartbeat measuring device in advance, and whether or not a valid heart rate has been measured may be determined by comparing the measured heart rate and a predefined threshold value.

However, since heart rates are different depending on the age, the stature, the weight, the sex, the exercise frequency, and the like of a user, there may be cases where an invalid heart rate is determined as being a normal value if a heart rate of another user is compared with the same threshold value. Therefore, even in this case, whether or not a measured heart rate is a normal value is preferably determined.

SUMMARY OF THE INVENTION

It is an aspect of the present application to provide a heartbeat measuring device and a heartbeat measuring method capable of determining whether or not a heartbeat measurement state is normal.

According to another aspect of the present application, there is provided a heartbeat measuring device including an information storage unit that stores unique information regarding a heart rate unique to a user or information regarding a detected heartbeat therein; and a determination unit that determines whether or not a heartbeat measurement state of the user is normal on the basis of the unique information or the information regarding a heartbeat, stored in the information storage unit.

The heartbeat measuring device may further include a threshold value calculation unit that calculates a threshold value of a heart rate for determining whether or not a heart rate of the user is a normal value on the basis of the unique information stored in the information storage unit.

In addition, the heartbeat measuring device may further include a measurement unit that measures a heart rate of the user, and the threshold value calculation unit may calculate the threshold value on the basis of the unique information and the heart rate measured by the measurement unit.

In addition, the threshold value calculation unit may calculate the threshold value on the basis of the unique information and an average value of a plurality of heart rates measured by the measurement unit for each specific time.

The unique information may include at least one of an exercise frequency and an exercise event of the user. Here, the threshold value calculation unit may calculate the number of measurements for obtaining the average value of heart rates on the basis of at least one of the exercise frequency and the exercise event of the user, and calculate the threshold value on the basis of an average value of heart rates measured over the number of measurements and the unique information.

In addition, the measurement unit may calculate a heart rate according to a pulse interval of an electrocardiogram signal from the user, compare a first value which is the calculated heart rate and a second value which is an integral multiple of the heart rate with a previously measured heart rate among a plurality of heart rates measured by the measurement unit for each specific time, and output a value closer to the previously measured heart rate of the first value and the second value as a measured heart rate.

The unique information may include at least one of a stable heart rate and a maximal heart rate of the user. Here, the threshold value calculation unit may calculate an upper limit threshold value of a heart rate which is a normal value on the basis of the maximal heart rate when the maximal heart rate is included in the unique information, and calculate a lower limit threshold value of the heart rate which is a normal value on the basis of the stable heart rate when the stable heart rate is included in the unique information.

In addition, the determination unit may compare the heart rate measured by the measurement unit with the threshold value calculated by the threshold value calculation unit, and determine whether or not the heart rate is a normal value.

In addition, the heartbeat measuring device may further include a notification unit that performs a notification when it is determined by the determination unit that the heart rate is not a normal value.

The notification unit may perform a notification when a heart rate measured after a specific time period has elapsed from starting measurement of a heart rate of the user by the measurement unit is determined as not being a normal value by the determination unit.

In addition, the heartbeat measuring device may further include an input unit that receives an input of the unique information and stores the input unique information in the information storage unit.

The heartbeat measuring device may further include a mounting unit for mounting the heartbeat measuring device on the arm of the user.

The heartbeat measuring device may further include an abnormality detection unit that detects abnormality from a heart rate measured by the measurement unit which measures the heart rate of the user; and a notification unit that performs a notification when abnormality is detected by the abnormality detection unit.

In addition, the notification unit may change information to be notified on the basis of a result detected by the abnormality detection unit.

The abnormality detection unit may detect poor mounting of the heartbeat measuring device on the basis of a plurality of heart rates measured by the measurement unit.

In addition, the abnormality detection unit may determine poor mounting when a predetermined frequency of signals exceeding a predetermined ratio or value with respect to an average value during a predetermined latest time period is detected.

The heartbeat measuring device may further include a communication unit that receives a signal indicating a heartbeat using wireless communication. Here, the abnormality detection unit may detect interference due to noise from outside on the basis of a plurality of signals received by the communication unit.

In addition, the abnormality detection unit may determine interference due to noise from outside when heart rates of a predefined value or more are measured to be more than a predetermined frequency.

Further, the abnormality detection unit may determine interference due to continuous noise from outside when continuous signals are received by the communication unit for a predefined time or more.

According to another aspect of the present application, there is provided a heartbeat measuring method causing a heartbeat measuring device which measures a heart rate of a user to perform storing unique information regarding a heart rate unique to a user or information regarding a detected heartbeat; and determining whether or not a heart rate measurement state of the user is normal on the basis of the unique information or the information regarding a heartbeat.

As described above, since information is stored, and it is determined whether or not a heartbeat measurement state of a user is normal on the basis of the information, it is possible to determine whether or not the heartbeat measurement state of the user is normal.

BRIEF DESCRIPTION OF THE DRAWINGS

FIGS. 4A and 4B are diagrams illustrating an example of the threshold value calculated according to the first embodiment of the present invention.

DETAILED DESCRIPTION OF THE INVENTION

Hereinafter, embodiments of the present invention will be described with reference to the drawings.

First Embodiment

First, the first embodiment of the present invention will be described.

Figure 1:
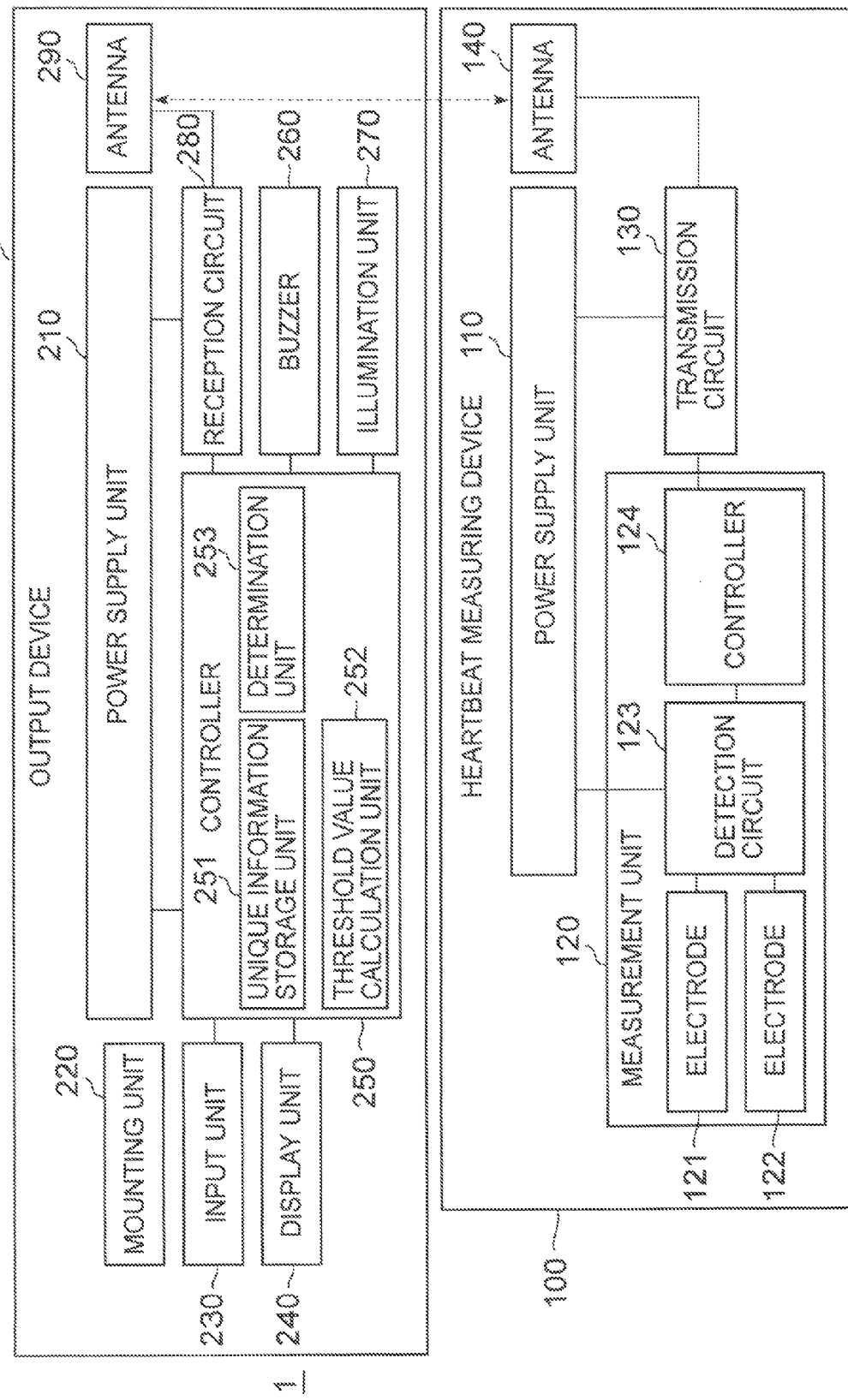
FIG. 1 is a block diagram illustrating a configuration example of the heartbeat measuring system according to a first embodiment of the present invention.
Figure 2:
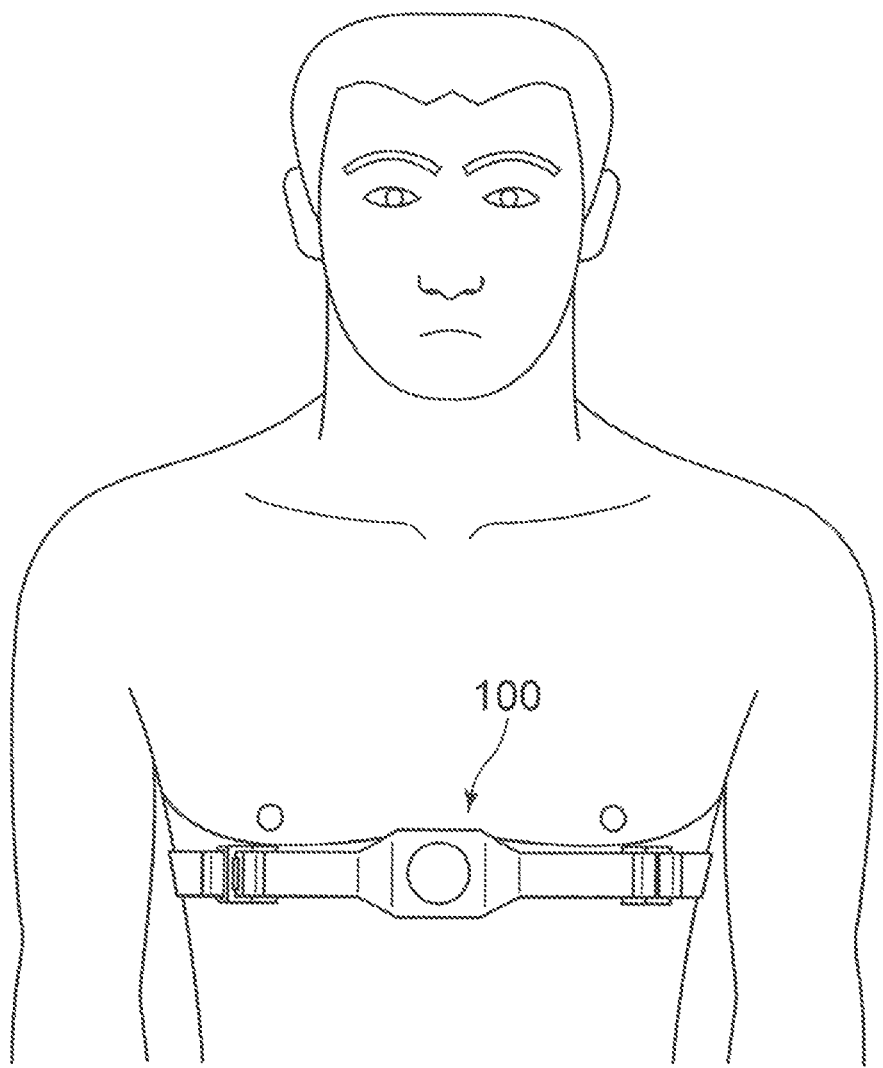
FIG. 2 is a diagram illustrating an exterior of a heartbeat measuring device according to the first embodiment of the present invention.
Figure 3:
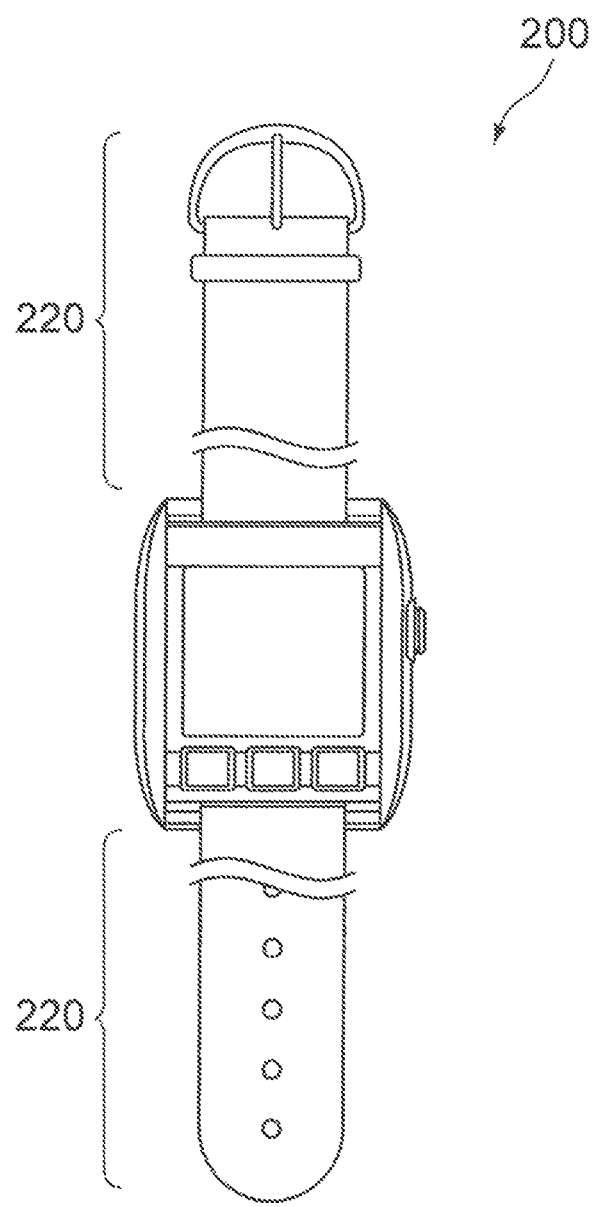
FIG. 3 is a diagram illustrating an exterior of an output device according to the first embodiment of the present invention.

FIG. 1 is a block diagram illustrating a configuration of a heartbeat measuring system 1 according to the present embodiment. The heartbeat measuring system 1 includes a heartbeat measuring device 100 and an output device 200. FIG. 2 is a diagram illustrating an exterior of the heartbeat measuring device 100. As shown in the figure, the heartbeat measuring device 100 is formed substantially in a ring shape so as to be mounted over the entire circumference of the chest of a user. The heartbeat measuring device 100 is mounted on the user's chest with the belt, detects an electrocardiogram signal occurring due to the heartbeat by making a pair of electrodes come into contact with the chest (living body surface) of the body, and calculates a heart rate on the basis of a detected electrocardiogram signal. FIG. 3 is a diagram illustrating an exterior of the output device 200. As shown in the figure, the output device 200 is a wrist watch type device, and is mounted on the user's wrist (arm) with the belt. The output device 200 is formed substantially in a ring shape so as to be mounted over the entire circumference of the user's wrist.

Referring to FIG. 1 again, the heartbeat measuring device 100 includes a power supply unit 110, a measurement unit 120, a transmission circuit 130, and an antenna 140.

The power supply unit 110 supplies power to each unit included in the heartbeat measuring device 100.

The measurement unit 120 has an electrode 121, an electrode 122, a detection circuit 123, and a controller 124, and measures a heart rate of the user for each specific time and outputs the measured heart rate.

The electrode 121 and the electrode 122 form a pair of electrodes, and detect an electrocardiogram signal occurring due to the heartbeat.

The detection circuit 123 outputs the electrocardiogram signal detected by the electrode 121 and the electrode 122 to the controller 124.

The controller 124 controls each unit included in the heartbeat measuring device 100. In addition, the controller 124 calculates a heart rate according to a pulse interval of the electrocardiogram signal output from the detection circuit 123, and outputs the calculation result as a result of measuring a heart rate. Here, the pulse interval of the electrocardiogram signal is, for example, an interval between peaks of the electrocardiogram signal. In addition, the controller 124 stores a heart rate which is measured for each specific time in a storage region thereof. A method of the controller 124 calculating a heart rate will be described later.

The transmission circuit 180 transmits the heart rate measured by the measurement unit 120 to the output device 200 via the antenna 140.

The antenna 140 performs wireless communication and transmits the heart rate measured by the measurement unit 120 to an antenna 290 of the output device 200.

The output device 200 includes a power supply unit 210, a mounting unit 220, an input unit 230, a display unit 240, a controller 250, a buzzer 260, an illumination unit 270, a reception circuit 280, and the antenna 290.

The power supply unit 210 supplies power to the respective units other than the mounting unit 220, included in the output device 200.

The mounting unit 220 is a belt for mounting the output device 200 on the user's arm.

The input unit 230 receives an operation input from the user. For example, the input unit 230 receives an input of unique information (or, also referred to as information) regarding a heart rate unique to the user, and stores the input unique information in a unique information storage unit (information storage unit) 251 of the controller 250. The unique information refers to information unique to the user such as, for example, a stable heart rate, a maximal heart rate, the age, the sex, the stature, the weight, the exercise frequency, and the exercise event of the user.

The display unit 240 is a display for displaying information.

The controller 250 controls the respective units included in the output device 200. Further, the controller 250 has the unique information storage unit 251, a threshold value calculation unit 252, and a determination unit 253, and determines whether or not a heart rate is a normal value as the kind of a heart rate measurement state not being normal on the basis of the unique information input to the input unit 230 and the heart rate transmitted from the heartbeat measuring device 100.

The unique information storage unit 251 stores the unique information input to the input unit 230.

The threshold value calculation unit 252 calculates a threshold value of a heart rate for determining whether or not a heart rate of the user is a normal value on the basis of the unique information stored in the unique information storage unit 251. In addition, the threshold value calculation unit 252 calculates a threshold value of a heart rate on the basis of the unique information stored in the unique information storage unit 251 and the heart rate measured by the measurement unit 120. For example, when a maximal heart rate is included in the unique information, the threshold value calculation unit 252 calculates an upper limit threshold value of a heart rate which is a normal value on the basis of the maximal heart rate, and when a stable heart rate is included in the unique information, the threshold value calculation unit 252 calculates a lower limit threshold value of the heart rate which is a normal value on the basis of the stable heart rate. Further, the threshold value calculation unit 252 stores the calculated, threshold value in storage region thereof.

FIGS. 4A and 4B are diagrams illustrating an example of the upper limit and lower limit threshold values calculated by the threshold value calculation unit 252. In these figures, FIG. 4A shows an example of the threshold value set in a specific range from a current heart rate, and FIG. 4B shows an example of the threshold value set based on the unique information.

In the example of FIG. 4A, the current heart rate is used as a reference value, and a predetermined multiple (±25%) of the reference value is set as a threshold value. For example, in a case where a heart rate calculated by the controller 124 is 120 (bpm), the threshold value calculation unit 252 calculates 150 (bpm) which is 125% of the heart rate as an upper limit threshold value, and calculates 90 (bpm) which is 75% of the heart rate as a lower limit threshold value. However, in this case, for example, in a case where a heart rate calculated by the controller 124 is 170 (bpm), an upper limit threshold value which is 125% of the heart rate is 213 (bpm). Here, it is said that a maximal heart rate is generally (220-value of the age), and, for example, in a case of being 20 years old, a maximal heart rate is about 200 (bpm). In other words, there is a high probability that the value 213 (bpm) may not be appropriate as a threshold value for determining whether or not a heart rate is normal.

Therefore, as shown in the example of FIG. 4B, the threshold value calculation unit 252 calculates an upper limit threshold value and a lower limit threshold value on the basis of the unique information stored in the unique information storage unit 251. For example, a value ((current heart rate+maximal heart rate)/2) obtained by dividing a sum of a current heart rate calculated by the controller 124 and a maximal heart rate by 2 is calculated as an upper limit threshold value. In addition, a value ((current heart rate+stable heart rate)/2) obtained by dividing a sum of a current heart rate calculated by the controller 124 and a stable heart rate by 2 is calculated as a lower limit threshold value. The figure shows a case where a stable heart rate is 60 (bpm), and a maximal heart rate is 180 (bpm). In this case, when a current heart rate is 120 (bpm), an upper limit threshold value is ((120+180)/2)=150 (bpm), and a lower limit threshold value is ((120+60)/2)=90 (bpm). When a current heart rate is 170 (bpm), an upper limit threshold value is ((170+180)/2)=175 (bpm) and a lower limit threshold value is ((170+60)/2)=115 (bpm). As such, it is possible to calculate an appropriate threshold value by using the unique information of the user.

The determination unit 253 determines whether or not a heart rate is a normal value by comparing the heart rate measured by the measurement unit 120 with a threshold value calculated by the threshold value calculation unit 252. For example, the determination unit 253 determines that a heart rate is not a normal value if the heart rate measured by the measurement unit 120 is larger than an upper limit threshold value calculated by the threshold value calculation unit 252. The determination unit 253 determines that a heart rate is a normal value if the heart rate measured by the measurement unit 120 is equal to or smaller than an upper limit threshold value calculated by the threshold value calculation unit 252 and equal to or larger than a lower limit threshold value calculated by the threshold value calculation unit 252. The determination unit 253 determines that a heart rate is not a normal value if the heart rate measured by the measurement unit 120 is smaller than a lower limit threshold value calculated by the threshold value calculation unit 252.

In addition, when the determination unit 253 determines that a heart rate transmitted from the heartbeat measuring device 100 is not a normal value, the controller 250 performs a notification thereof. For example, the controller 250 may perform the notification by making the display unit 240 display marks indicating warning or by making the buzzer 260 emit a warning sound.

Here, when the notification is performed, the controller 250 may take into consideration the elapsed time from starting of measurement. For example, immediately after the user mounts the heartbeat measuring device 100 thereon, the closeness between the heartbeat measuring device 100 and the user's skin is not good, and thus an electrocardiogram signal may not be normally detected. For example, when the heartbeat measuring device 100 gets wet by the user sweating or the like, an electrocardiogram signal may be normally detected. Therefore, the controller 250 performs control so as not to perform a notification even if a heart rate which is not a normal value is detected during a warm-up period which is a specific time period (for example, five minutes) after the heartbeat measuring device 100 starts measuring a heart rate. In other words, if the measurement unit 120 starts measuring a heart rate of the user, the controller 250 starts measuring using a warm-up timer using a clocking function thereof, and performs a notification in a case where the determination unit 253 determines that a heart rate measured after the specific time period has elapsed is not a normal value. Alternatively, for example, a mark indicating the notification may be displayed during the warm-up period, and a mark indicating that the warm up is in progress may also be displayed. Thereby, it is possible to notify the user of a probability that a heart rate may not be a normal value since the warm up is in progress.

The buzzer 260 is a speaker emitting sound. For example, the buzzer 260 is a notification unit which emits notification sound when the determination unit 253 determines that a heart rate is not a normal value.

The illumination unit 270 illuminates the display unit 240 with light such that the user can visually recognize the display unit 240 even in a dark place.

The reception circuit 280 receives a heart rate transmitted from the heartbeat measuring device 100 via the antenna 290.

The antenna 290 performs wireless communication and receives a heart rate measured by the measurement unit 120 of the heartbeat measuring device 100 from the antenna 140 of the heartbeat measuring device 100.

Figure 5:
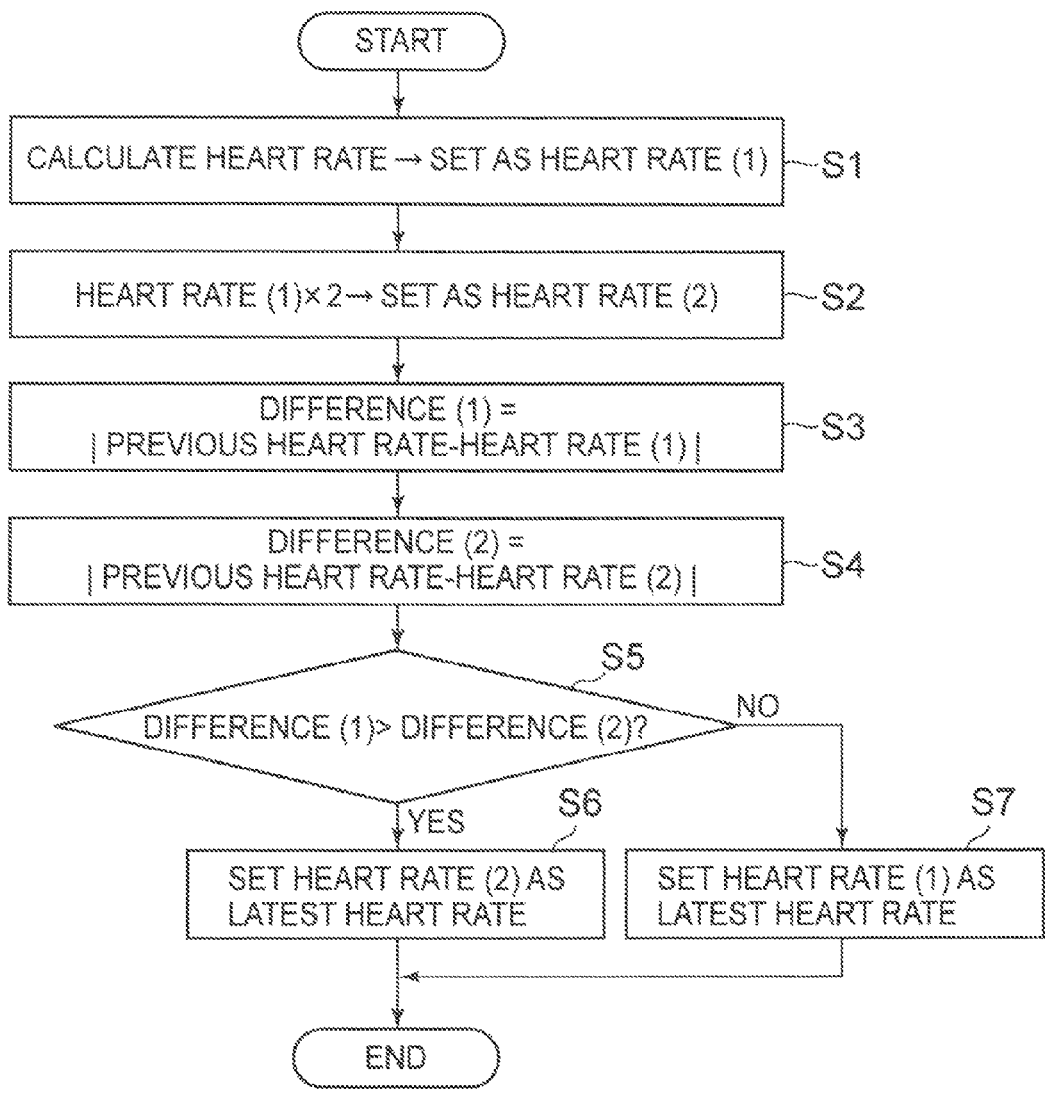
FIG. 5 is a flowchart illustrating an example of the heart rate calculation process according to the first embodiment of the present invention.

Next, with reference to the drawings, an operation example of the heartbeat measuring system 1 according to the first embodiment will be described. FIG. 5 is a flowchart illustrating an operation example where the measurement unit 120 according to the first embodiment measures a heart rate.

When the detection circuit 123 outputs an electrocardiogram signal detected by the electrode 121 and the electrode 122, the controller 124 calculates a heart rate (1) on the basis of a pulse interval of the electrocardiogram signal (step S1). The controller 124 calculates a heart rate (2) by doubling the calculated heart rate (1) (step S2). The controller 124 calculates a difference (1) which is an absolute value of a difference between a previous heart rate and the heart rate (1) (step S3). In addition, the controller 124 calculates a difference (2) which is an absolute value of a difference between the previous heart rate and the heart rate (2) (step S4).

Here, the previous heart rate may employ, for example, a previous heart rate among a plurality of heart rates which are measured for each specific time after the measurement unit 120 starts measuring a heart rate, or may be an average value of a plurality (N) (where N is a positive integer) of heart rates. A value of N may be optimized depending on an exercise frequency of the user. For example, a person for which an exercise frequency is high has relatively fast rising or falling in a heart rate, and thus a small value is appropriate as N. On the other hand, a person for which an exercise frequency is low has relatively slow rising and falling in a heart rate, and thus a large value may be set as N. In addition, a value of N may be set depending on an exercise event. For example, in a case of an event such as a marathon where a heart rate does not frequently vary, N may be set to a large value. In contrast, for example, in a case of an event such as soccer where a heart rate repeats rapid rising and rapid falling, N is preferably set to a small value.

Here, the reason why the controller 124 calculates the heart rate (2) which is twice the heart rate (1) is that, in a case where detection of an electrocardiogram signal is omitted, a detection frequency becomes about a half thereof, and thus a value of the heart rate (1) becomes about a half of the original value. In this case, by doubling the heart rate (1), it is possible to correct a value of the heart rate. In other words, the controller 124 calculates a heart rate according to a pulse interval of an electrocardiogram signal detected from the user by the detection circuit 123, compares a first value which is the calculated heart rate and a second value which is an integral multiple of the heart rate with a previously measured heart rate among a plurality of heart rates measured for each specific time by the measurement unit 120, and outputs a value closer to the measured heart rate of the first value and the second value as a measured heart rate. In other words, in a case where a value of a previous heart rate and a value of a newly calculated heart rate are abnormally separated from each other, this is regarded as a detecting error, and thus a more reliable value is calculated as the heart rate (2). Here, although an example where the heart rate (1) is doubled is shown, a value which is an integral multiple such as three times or four times the heart rate may be calculated as the heart rate (2) and be compared in the same manner.

The controller 124 compares the difference (1) with the difference (2) (step S5). If it is determined that the difference (1) is larger than the difference (2) (step S5: YES), the controller 124 outputs the heart rate (2) as the latest heart rate (step S6). On the other hand, if it is determined that the difference (1) is not larger than the difference (2) (step S5: NO), the controller 124 outputs the heart rate (1) as the latest heart rate (step S7).

Figure 6:
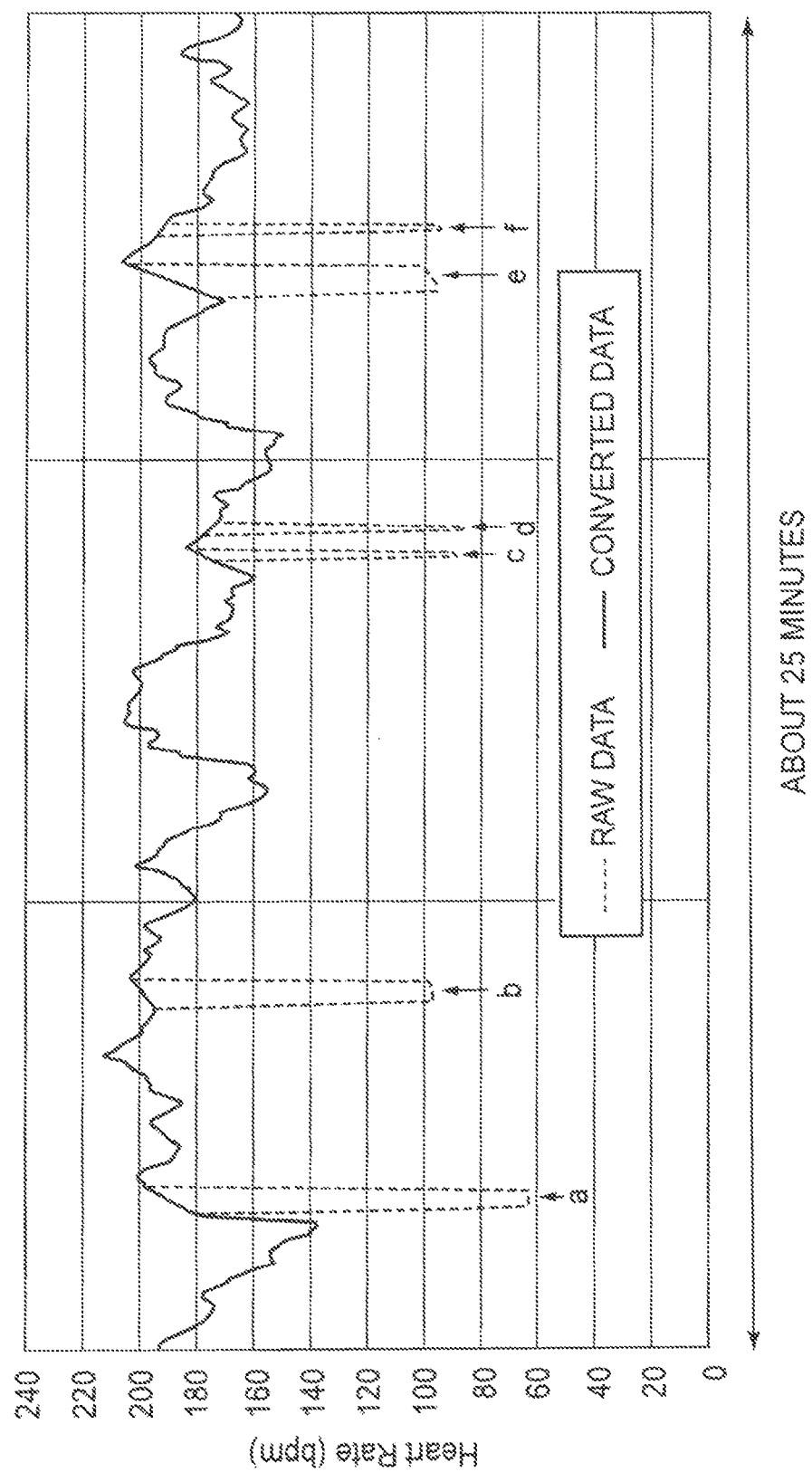
FIG. 6 is a diagram illustrating an example of the heart rate calculated according to the first embodiment of the present invention.

FIG. 6 is a diagram illustrating an example of the heart rate according to the first embodiment of the present invention. In the figure, the raw data indicated by the broken lines is the heart rate (1) calculated based on a pulse interval of an electrocardiogram signal measured by the detection circuit 123. The heart rate (1) shows a rapidly decreasing value at each location of the reference signs a to f. These rapid variations in the heart rate may be caused by detection omission of an electrocardiogram signal. Therefore, a value of the heart rate is corrected by taking an integral multiple (twice) of the calculated heart rate. In the figure, converted data indicated by the solid line shows transition of a heart rate corrected in this way.

Figure 7:
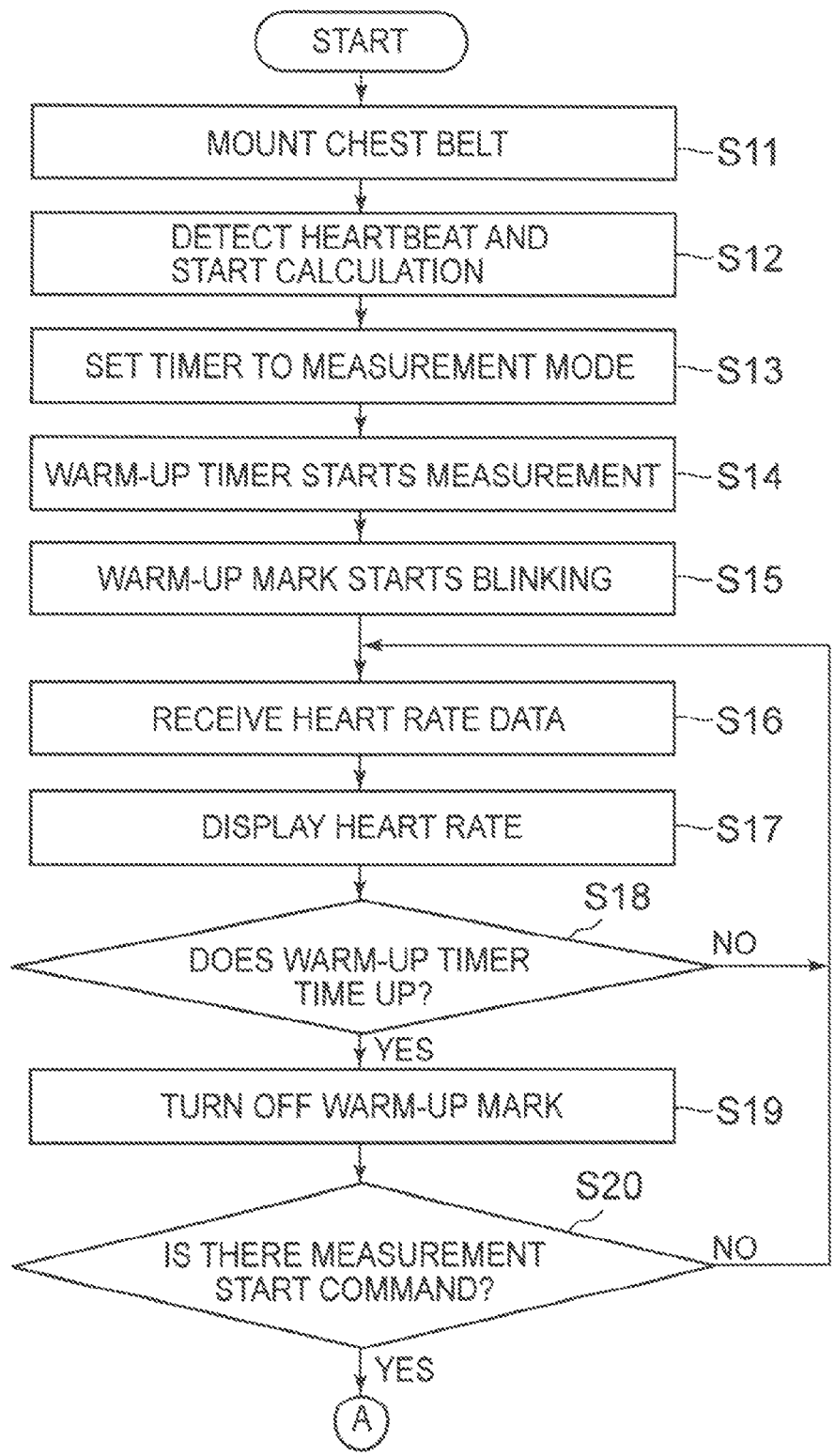
FIG. 7 is a flowchart illustrating an example of the measurement process according to the first embodiment of the present invention.
Figure 8:
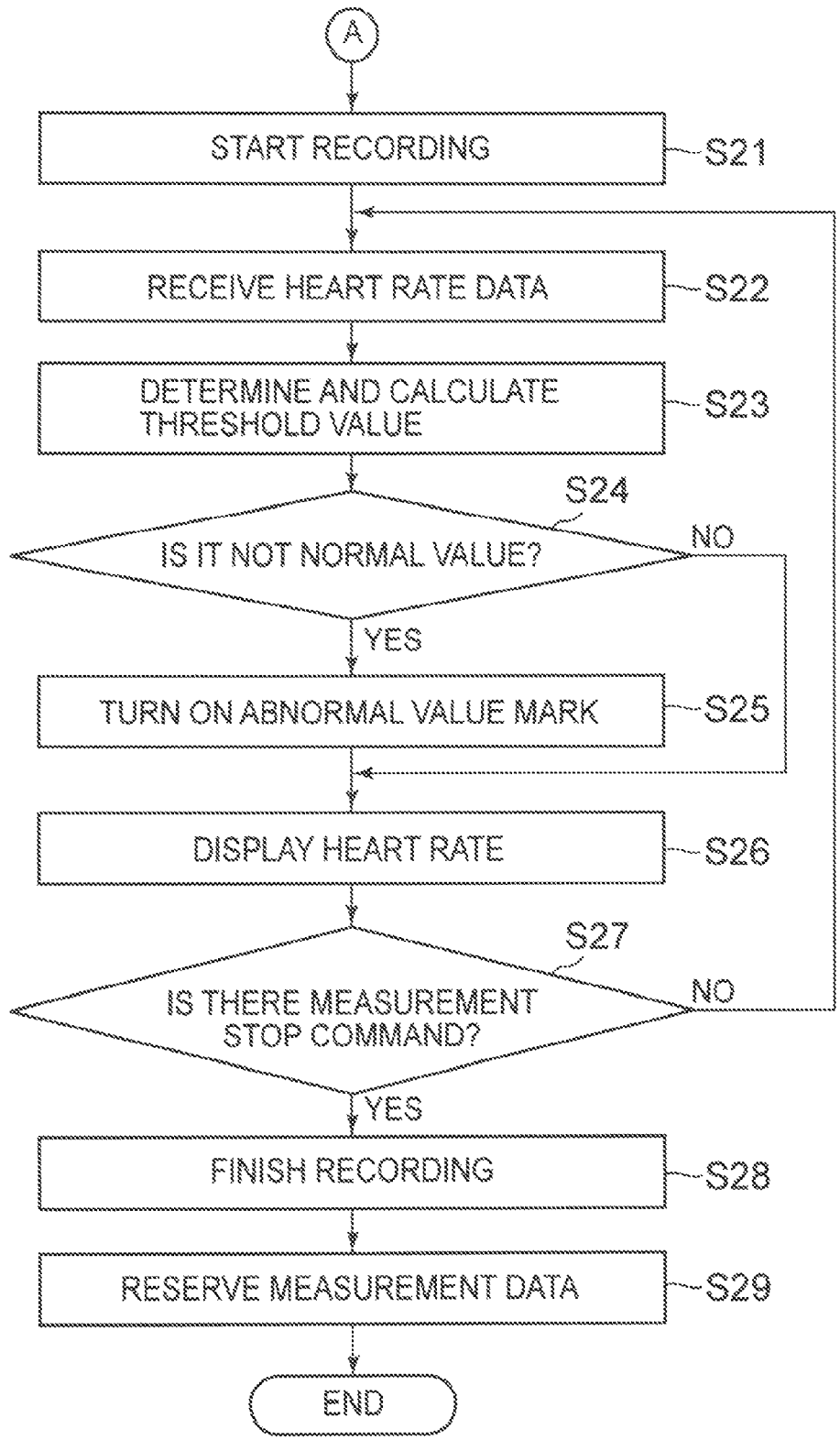
FIG. 8 is a flowchart illustrating an example of the measurement process according to the first embodiment of the present invention.

FIGS. 7 and 8 are flowcharts illustrating an operation example where the heartbeat measuring system 1 according to the first embodiment measures a heart rate. Here, it is assumed that unique information is input to the output device 200 from the user in advance so as to be stored in the unique information storage unit 251, a threshold value is calculated by the threshold value calculation unit 252 on the basis of the unique information, and the threshold value is stored in a storage region of the threshold value calculation unit 252.

When the user mounts the heartbeat measuring device 100 (chest belt) thereon (step S11), the measurement unit 120 detects an electrocardiogram signal and measures a heart rate (step S12). The transmission circuit 130 of the heartbeat measuring device 100 transmits the heart rate measured by the measurement unit 120 to the output device 200 via the antenna 140. The user mounts the output device 200 (watch) on his/her arm and inputs a start command of a measurement mode into the input unit 230. When the start command of the measurement mode is input to the input unit 230 (step S13), the controller 250 starts measurement using the warm-up timer (step S14), and displays a mark indicating the starting of the warm-up measurement on the display unit 240 (step S15).

When the reception circuit 280 of the output device 200 receives the heart rate transmitted from the heartbeat measuring device 100 via the antenna 290 (step S16), the controller 250 displays the received heart rate on the display unit 240 (step S17). The controller 250 determines whether or not a set time has elapsed using the warm-up timer starting in step S14 (step S18). If it is determined that the set time has not elapsed using the warm-up timer (step S18: NO), the controller 250 returns the flow to step S16. On the other hand, if it is determined that the set time has elapsed using the warm-up timer (step S18: YES), the controller 250 turns off the warm-up mark which is displayed on the display unit 240 (step S19).

If a measurement start command is not input to the input unit 230 (step S20: NO), the controller 250 returns the flow to step S16. When the measurement start command is input to the input unit 230 (step S20: YES), the flow proceeds to FIG. 8, and the controller 250 starts a process of recording a heart rate (step S21). When the controller 250 receives the heart rate transmitted from the heartbeat measuring device 100 (step S22), the determination unit 253 reads the threshold value stored in the threshold value calculation unit 252 and compares the heart rate received from the heartbeat measuring device 100 with the threshold value read from the threshold value calculation unit 252 (step S23).

If the determination unit 253 determines that the heart rate is not a normal value (step S24: NO), the controller 250 performs a notification thereof. For example, the controller 250 displays a mark indicating that the heart rate is an abnormal value on the display unit 240 (step S25). On the other hand, if the determination unit 253 determines that the heart rate is a normal value (step S24: YES), the flow proceeds to step S26.

The determination unit 253 displays the heart rate received from the heartbeat measuring device 100 on the display unit 240 (step S26).

If a measurement stop command is not input to the input unit 230 (step S27: NO), the flow returns to step S22, and the output device 200 continuously performs the measurement process. If the measurement stop command is input to the input unit 230 (step S27: YES), the controller 250 finishes the threshold value determination process and the like (step S28), and stores the measured heart rate into the storage region of the controller 250 (step S29).

In addition, although, in the present embodiment, an example where the unique information of the user is input to the input unit 230 by the user has been described, the unique information of the user may be calculated by the output device 200. For example, in a case where a plurality of records regarding a heart rate of the user are stored in the storage region of the output device 200, the greatest heart rate may be determined as being a maximal heart rate, and the smallest heart rate may be set as a stable heart rate, from heart rate records. Alternatively, for example, a stable heart rate measurement function may be provided, and a heart rate of a user may be measured at the stable time when the user wakes up in the morning and may be stored as a stable heart rate. Alternatively, for example, an exercise frequency may be calculated using the number of measurements performed by the output device 200 as the number of exercises. Alternatively, an input of the age of a user may be received, and a value obtained by subtracting the age from 220 may be calculated as a maximal heart rate.

In addition, when the determination unit 253 compares a heart rate with a threshold value, the threshold value may be corrected based on a measurement time from starting of an exercise, an exercise event, or the like. For example, a heart rate may rapidly increase immediately after an exercise starts. Further, a user for which an exercise frequency is high exhibits a tendency for rapid heart rate increase after an exercise starts, and a user for which an exercise frequency is low exhibits a tendency for slow heart rate increase after an exercise starts. Furthermore, for example, in an exercise event such as a marathon, after a heart rate increases once, a high heart rate may be maintained stably, whereas, for example, in an exercise event such as soccer, a heart rate rapidly increases or rapidly decreases during the measurement. Depending on these tendencies, a threshold value may be corrected.

Further, although, in the present embodiment, the controller 250 regards the warm up as being finished if a specific time period has elapsed after a measurement starts, and starts measuring a heart rate, for example, the controller 250 may regard the warm up as being finished and start measuring a heart rate in a case where a heart rate measured by the heartbeat measuring device 100 is determined as being a normal value within upper and lower threshold values over a specific number of times or more.

In addition, although, in the present embodiment, an example where the functional unit for performing the process of measuring a heart rate or the like is distributed to and provided in the heartbeat measuring device 100 and the output device 200 has been described, the functional unit may be configured depending on usages or exercise events. For example, although, in the present embodiment, an example where the controller 124 of the heartbeat measuring device 100 calculates a heart rate on the basis of an electrocardiogram signal output from the detection circuit 123 has been described, the output device 200 may have the same function as the controller 124. In this case, the heartbeat measuring device 100 transmits an electrocardiogram signal output from the detection circuit 123 to the output device 200, and the controller 250 included in the output device 200 calculates a heart rate.

Alternatively, there may be a configuration in which the heartbeat measuring device 100 includes the determination unit 253 and stores a threshold value in advance, compares a heart rate measured by the measurement unit 120 with the threshold value, and transmits a determination result or a correction result to the output device 200.

Alternatively, a heart rate measured by the heartbeat measuring device 100 may be transmitted to an output device which is a PC (personal computer) which includes the unique information storage unit 251, the threshold value calculation unit 252, and the determination unit 233, without using the wrist watch type output device 200. In this case, for example, the output device which is the PC may perform a process such as calculation of a threshold value or comparison of a threshold value with a heart rate and summarize a process result using a graph or the like so as to be output.

As described above, according to the present embodiment, a threshold value of a heart rate is calculated based on unique information of a user, and thereby it is possible to calculate a unique threshold value according to the user. In addition, a measurement is made to start after the warm-up in consideration of many cases where there are detection errors of an electrocardiogram signal immediately after the heartbeat measuring device 100 is mounted, and thereby it is possible to prevent a heart rate based on detection errors from being output. Thereby, it is possible to calculate and output a heart rate with higher reliability.

Second Embodiment

Next, the second embodiment of the present invention will be described.

Figure 9:
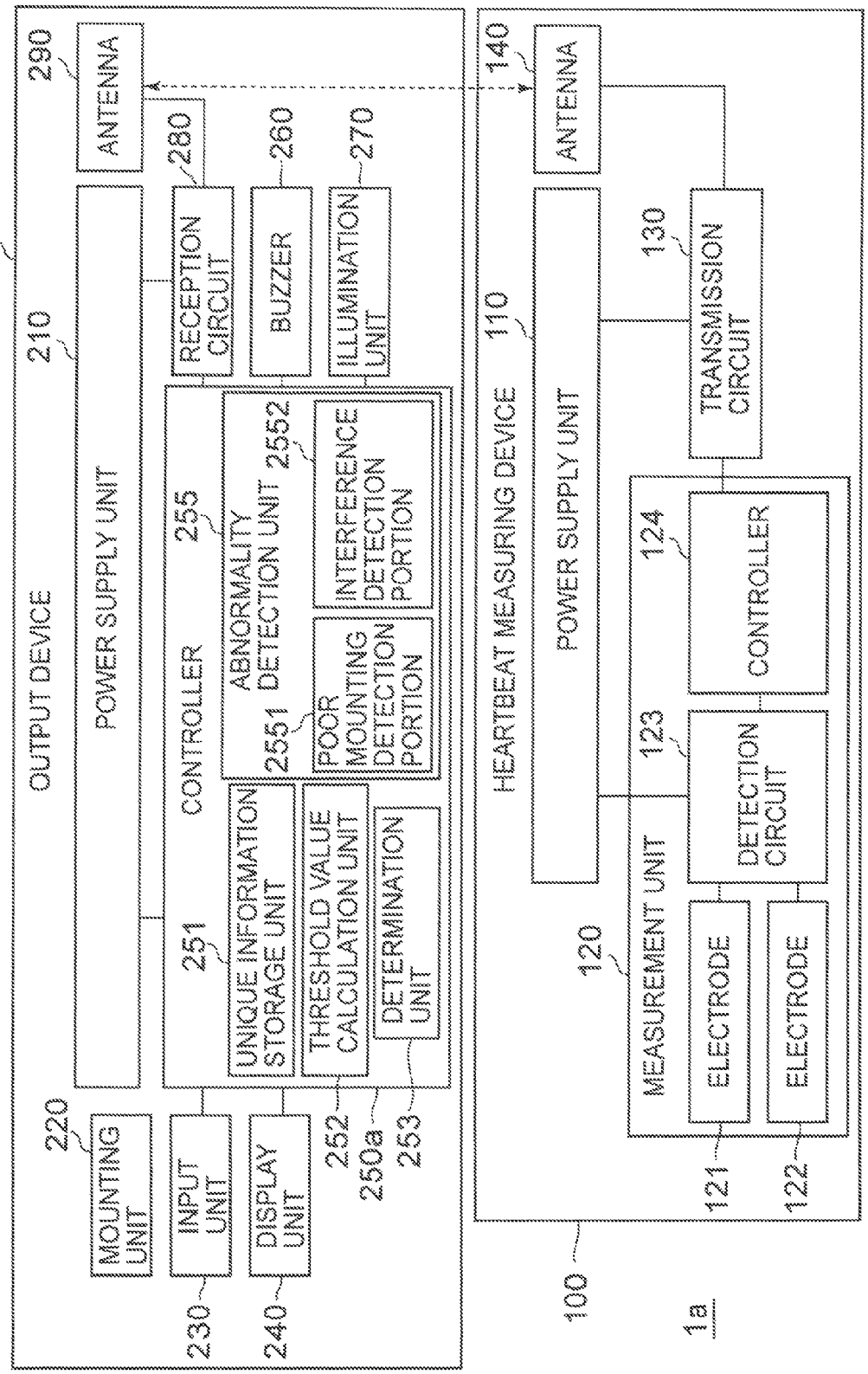
FIG. 9 is a block diagram illustrating a configuration example of the heartbeat measuring system according to a second embodiment of the present invention.

FIG. 9 is a block diagram illustrating a configuration example of the heartbeat measuring system 1a according to the present embodiment. A difference between the heartbeat measuring system 1a according to the present embodiment and the heartbeat measuring system 1 according to the first embodiment shown in FIG. 1 is that an output device 200a is provided instead of the output device 200. In addition, a heartbeat measuring device 100 according to the present embodiment transmits a heartbeat signal which is a detected electrocardiogram signal to the output device 200a. The heartbeat signal is a signal synchronized with a beat of a heart rate. Further, in the present figure, the same constituent elements as in the heartbeat measuring system 1 shown in FIG. 1 are given the same reference numerals, and description thereof will be omitted. The output device 200a discriminates poor mounting and interference as the kinds of heartbeat measurement states which are not normal, and performs a poor mounting notification and an interference notification. The output device 200a includes a controller 250a instead of the controller 250 of the output device 200 shown in FIG. 1. Further, a unique information storage unit 251 included in the output device 200a according to the present embodiment stores a threshold value for discriminating poor mounting and a threshold value for discriminating interference as information regarding a heartbeat. The controller 250a includes an abnormality detection unit 255 in addition to the configuration of the controller 250 shown in FIG. 1. In addition, the controller 250a calculates a heart rate on the basis of a heartbeat signal received from the heartbeat measuring device 100. The remaining configuration of the output device 200a is the same as the configuration of the output device 200 shown in FIG. 1.

The abnormality detection unit 255 detects noise (abnormality) from the heartbeat signal received from the heartbeat measuring device 100 on the basis of the threshold value stored in the unique information storage unit 251. The noise described here is a signal where a heart rate is not a normal value. The abnormality detection unit 255 includes a poor mounting detection portion 2551 and an interference detection portion 2552. The poor mounting detection portion 2551 detects poor mounting of the heartbeat measuring device 100 on the basis of the threshold value for discriminating poor mounting, stored in the unique information storage unit 251 and a plurality of measured heart rates. The poor mounting indicates a state in which an electrocardiogram signal cannot be normally detected due to a way of mounting the heartbeat measuring device 100. For example, as the poor mounting, there is a state in which a degree of adhesion between a user and the heartbeat measuring device 100 is low since tightening of the belt of the heartbeat measuring device 100 is poor, a state in which a mounted position of the heartbeat measuring device 100 is deviated, a state in which it is difficult for the heartbeat measuring device 100 to detect an electrocardiogram signal since the user's skin is dry, or the like. A method of detecting poor mounting will be described later in detail. The interference detection portion 2552 detects interference due to noise from outside (hereinafter, referred to as external noise) which is a signal transmitted from devices other than the heartbeat measuring device 100 on the basis of the threshold value for discriminating interference, stored in the unique information storage unit 251, and a plurality of heartbeat signals received by the reception circuit 280 via the antenna 290. For example, the interference detection portion 2552 determines interference due to isolated noise from outside in a case where heartbeat signals of a predefined value or more are measured to be more than a predefined frequency. Here, the predefined value and the predefined frequency are threshold values for discriminating interference, stored in the unique information storage unit 251. Further, the interference detection portion 2252 determines interference due to continuous noise from outside in a case where continuous signals are received by the reception circuit 280 for a predefined time or more. Here, the predefined time is a threshold value for discriminating interference, stored in the unique information storage unit 251. The reception circuit 280 and the antenna 290 are a communication unit which receives heartbeat signals measured by the measurement unit 120 of the heartbeat measuring device 100 with wireless communication. The communication unit receives a signal indicating a heartbeat using a burst signal. For this reason, in a case where there is a signal similar to the heartbeat signal in the vicinity of the output device 200a, the signal is also received, and thus interference occurs. A method of detecting interference will be described later in detail.

Figure 10:
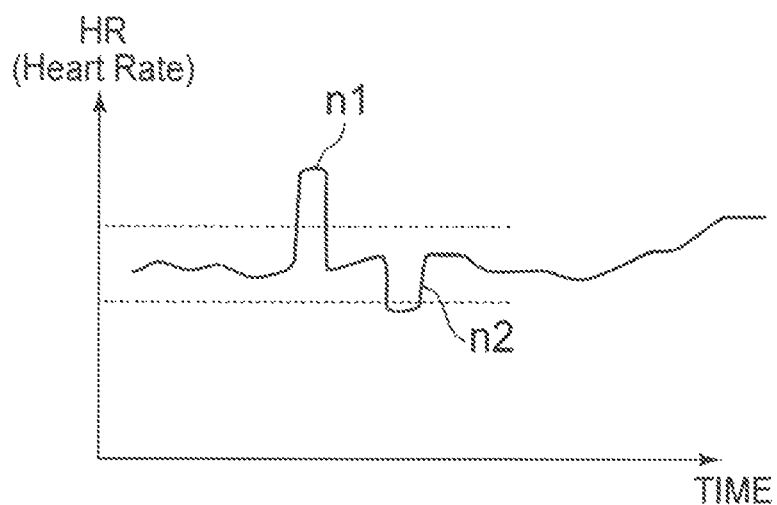
FIG. 10 is a diagram illustrating an example of the heart rate variations in a case of poor mounting, received by an output device according to the second embodiment of the present invention.

Next, a description will be made of a method of detecting poor mounting of the heartbeat measuring device 100. FIG. 10 is a diagram illustrating an example of heart rate variations in a case of poor mounting, received by the output device 200a according to the present embodiment. The longitudinal axis of the graph shown in the present figure expresses a heart rate (HR), and the transverse axis expresses time (Time). As shown in the present figure, for example, in a case where the heartbeat measuring device 100 is deviated with respect to the user's body since the user moves his/her upper body, the noise n1 is generated upward. In addition, in a case where a degree of adhesion between the user and the heartbeat measuring device 100 is not good, the noise n2 is generated downward. Further, in a case where the user's skin is dry and thus the reception sensitivity of the electrocardiogram signal is not good, at least one of the upward noise n1 and the downward noise n2 is generated. The poor mounting detection portion 2551 detects poor mounting on the basis of these noises n1 and n2. Specifically, the poor mounting detection portion 2551 determines poor mounting in a case where heart rates exceeding a predetermined ratio Y have more than a predetermined frequency Z with respect to an average value (movement average value) of directly adjacent X heart rates. The frequency is a ratio in directly adjacent $N_1$ heart rates. For example, the poor mounting detection portion 2551 determines poor mounting in a case where a frequency of heart rates larger than +25% with respect to the movement average value or a frequency of heart rates smaller than −25% with respect to the movement average value is equal to or more than 5% in directly adjacent twenty heart rates. Further, hereinafter, the number X of heart rates for obtaining a movement average value of heart rates is set to a movement average number X. Here, X, the predetermined ratio Y, and the predetermined frequency Z are threshold values for discriminating poor mounting, stored in the unique information storage unit 251. The poor mounting detection portion 2551 reads X, the predetermined ratio Y, and the predetermined frequency Z from the unique information storage unit 251, and detects poor mounting on the basis of the read values.

Figure 11:
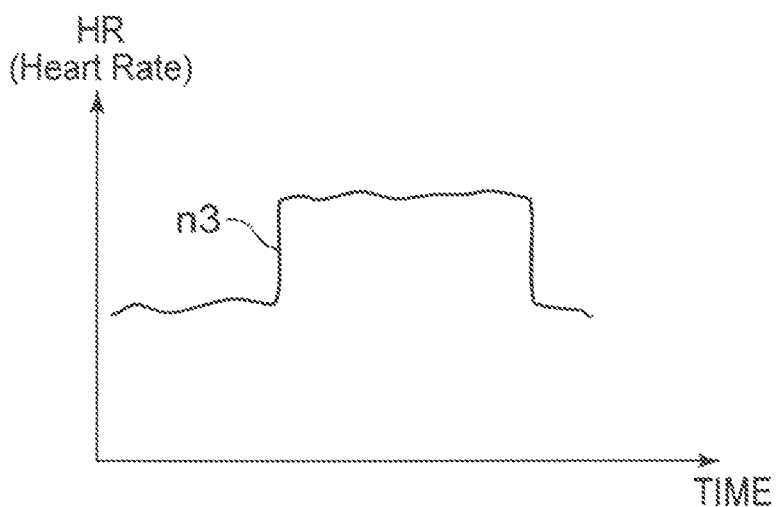
FIG. 11 is a diagram illustrating an example of the heart rate variations in a case of interference due to isolated external noise, received by the output device according to the second embodiment of the present invention.

Next, a method of detecting interference due to isolated external noise will be described. FIG. 11 is a diagram illustrating an example of heart rate variations in a case of interference due to isolated external noise, received by the output device 200a according to the present embodiment. The longitudinal axis of the graph shown in the present figure expresses a heart rate (HR), and the transverse axis expresses time (Time). Since the heartbeat measuring device 100 and the output device 200a perform wireless communication therebetween, when there is another heartbeat measuring device 100 around the output device 200a, the output device 200a also receives a heartbeat signal from another heartbeat measuring device 100. For this reason, when another user B using the same heartbeat measuring device 100 becomes closer to the user A, the output device 200a receives heartbeat signal from both the heartbeat measuring device 100 of the user A and the heartbeat measuring device 100 of the user B. Thereby, a heartbeat signal input to the controller 250a is a value close to a signal obtained by adding the heartbeat signal of the user A and the heartbeat signal of the user B. Therefore, when another user B using the same heartbeat measuring device 100 becomes closer to the user A, as in the present figure, the noise n3 with a value close to a signal obtained by adding the heartbeat signal of the user A to the heartbeat signal of the user B is generated. In addition, if another user B becomes distant from the user A, the noise n3 disappears. The interference detection portion 2552 detects interference due to isolated external noise on the basis of this noise n3. Specifically, the interference detection portion 2552 determines interference due to isolated external noise in a case where heart rates of a predetermined value α or more exceed a predetermined frequency β. The frequency is a ratio in directly adjacent $N_2$ heart rates. For example, the interference detection portion 2552 determines interference due to isolated external noise in a case where a frequency of heart rates of 300 (bpm) or more is equal to or more than 10% in a directly adjacent twenty data events. Here, the predetermined value α and the predetermined frequency β are threshold values for discriminating interference, stored in the unique information storage unit 251. The interference detection portion 2552 reads the predetermined value α and the predetermined frequency β from the unique information storage unit 251 and detects interference on the basis of the read values.

Figure 12A:
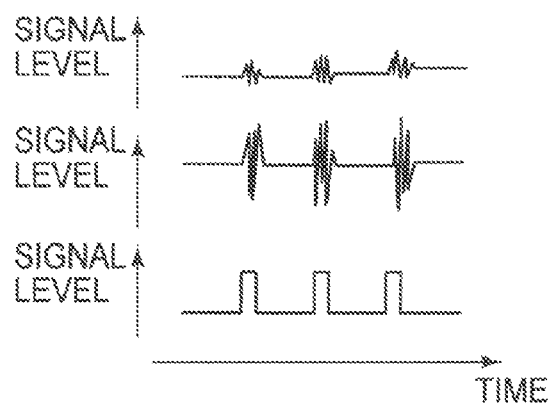
FIGS. 12A and 12B are diagrams illustrating an example of the heart rate in a case of interference due to continuous external noise, received by the output device according to the second embodiment of the present invention.
Figure 12B:
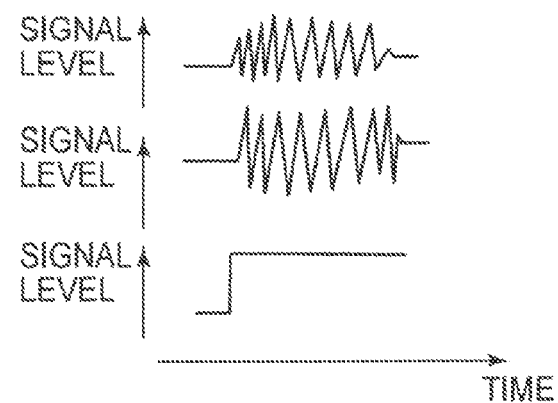

Next, a method of detecting interference due to continuous external noise will be described. FIGS. 12A and 12B are diagrams illustrating an example of the heart rate in a case of interference due to continuous external noise, received by the output device 200a according to the present embodiment. The longitudinal axis of the graphs shown in the present figures expresses a signal level (voltage or the like), and the transverse axis expresses time (Time). FIG. 12A shows a heartbeat signal in a normal state (a state where there is no noise). FIG. 12B shows a heartbeat signal in a case where there is continuous external noise. Here, the reception circuit 280 includes an amplifying filter and a comparator. Further, the controller 250a includes a CPU (Central Processing Unit) and processes a signal which is received by the reception circuit 280 via the antenna 290. Specifically, first, the amplifying filter amplifies a received signal. Next, the comparator binarizes the amplified signal. In addition, the CPU calculates a heart rate on the basis of rising or falling of the binarized signal. Each signal shown on the upper side of FIGS. 12A and 12B is a signal which is received by the reception circuit 280 via the antenna 290 and is input to the amplifying filter. In addition, each signal shown on the intermediate side of FIGS. 12A and 12B is a signal which is amplified by the amplifying filter and is input to the comparator. Further, each signal shown on the lower side of FIGS. 12A and 12B is a signal which is binarized by the comparator and is input to the CPU.

When a running user who mounts the heartbeat, measuring system 1a thereon passes by a device such as a railroad crossing which generates continuous signals, the reception circuit 280 receives continuous signals as shown on the upper side of FIG. 12B via the antenna 290. As a result, a signal which is binarized and is input to the CPU does not have a pulse form and falling as shown on the lower side of FIG. 12B (a high state continues). This state is determined as being no signals by the CPU, but, actually, is a state where there are continuous signals. The interference detection portion 2552 determines this state as being a state where continuous external noise interferes. Specifically, the interference detection portion 2552 determines interference due to continuous external noise in a case where continuous signals are received by the reception circuit 280 for a predetermined time T or more (in a case where a high state of the signals continues for the predetermined time T or more). Here, the predetermined time is a threshold value for discriminating interference, stored in the unique information storage unit 251. The interference detection portion 2552 reads the predetermined time T from the unique information storage unit 251 and detects interference on the basis of the read value.

Figure 13:
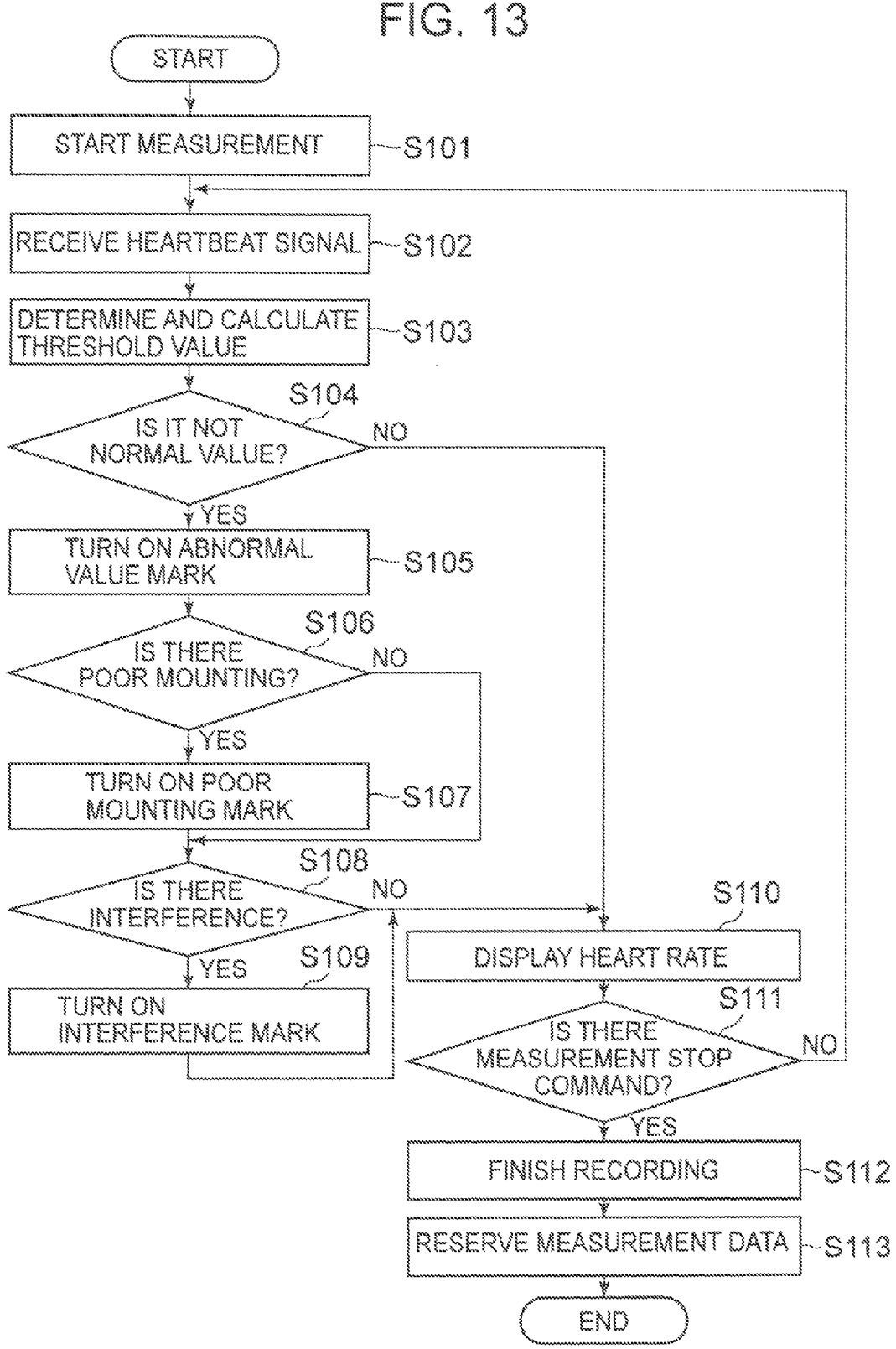
FIG. 13 is a flowchart illustrating an example of the measurement process according to the second embodiment of the present invention.

Next, with reference to the drawing, an operation example of the heartbeat measuring system 1a according to the present embodiment will be described. FIG. 13 is a flowchart illustrating an example of the measurement process according to the present embodiment.

The controller 250a (notification unit) starts measurement when a measurement start command is input to the input unit 230 (step S101).

The controller 250a receives a heartbeat signal transmitted from the heartbeat measuring device 100 and calculates a heart rate using the received heartbeat signal (step S102). After the reception, the flow proceeds to step S103.

The determination unit 253 reads a threshold value stored in the threshold value calculation unit 252, and compares the heart rate calculated by the controller 250a with the threshold value read from the threshold value calculation unit 252 (step S103).

The determination unit 253 determines whether or not the heart rate is a normal value on the basis of the comparison result (step S104).

If the determination unit 253 determines that the heart rate is not a normal value (step S104: NO), the controller 250a makes the process proceed to step S105. On the other hand, if the determination unit 253 determines that the heart rate is a normal value (step S104: YES), the controller 250a makes the process proceed to step S110.

The controller 250a displays a mark indicating that the heart rate is an abnormal value on the display unit 240 (step S105).

Next regarding step S105, the poor mounting detection portion 2551 determines whether or not there is poor mounting (step S106). If the poor mounting detection portion 2551 determines that there is poor mounting (step S106: YES), the controller 250a performs a notification thereof. For example, the controller 250a displays a mark indicating that there is poor mounting on the display unit 240 (step S107). On the other hand, if the poor mounting detection portion 2551 determines that there is no poor mounting (step S106: NO), the flow proceeds to step S108.

Next, the interference detection portion 2552 determines whether or not there is interference (step S108). If the interference detection portion 2552 determines that there is interference (step S108: YES), the controller 250a performs a notification thereof. For example, the controller 250a displays a mark indicating that there is interference on the display unit 240 (step S109). On the other hand, if the interference detection portion 2552 determines that there is no interference (step S108: NO), the flow proceeds to step S110.

The subsequent processes in steps S110 to S113 are the same as the above-described processes in steps S26 to S29 (refer to FIG. 8) and thus description thereof will be omitted.

Figure 14:
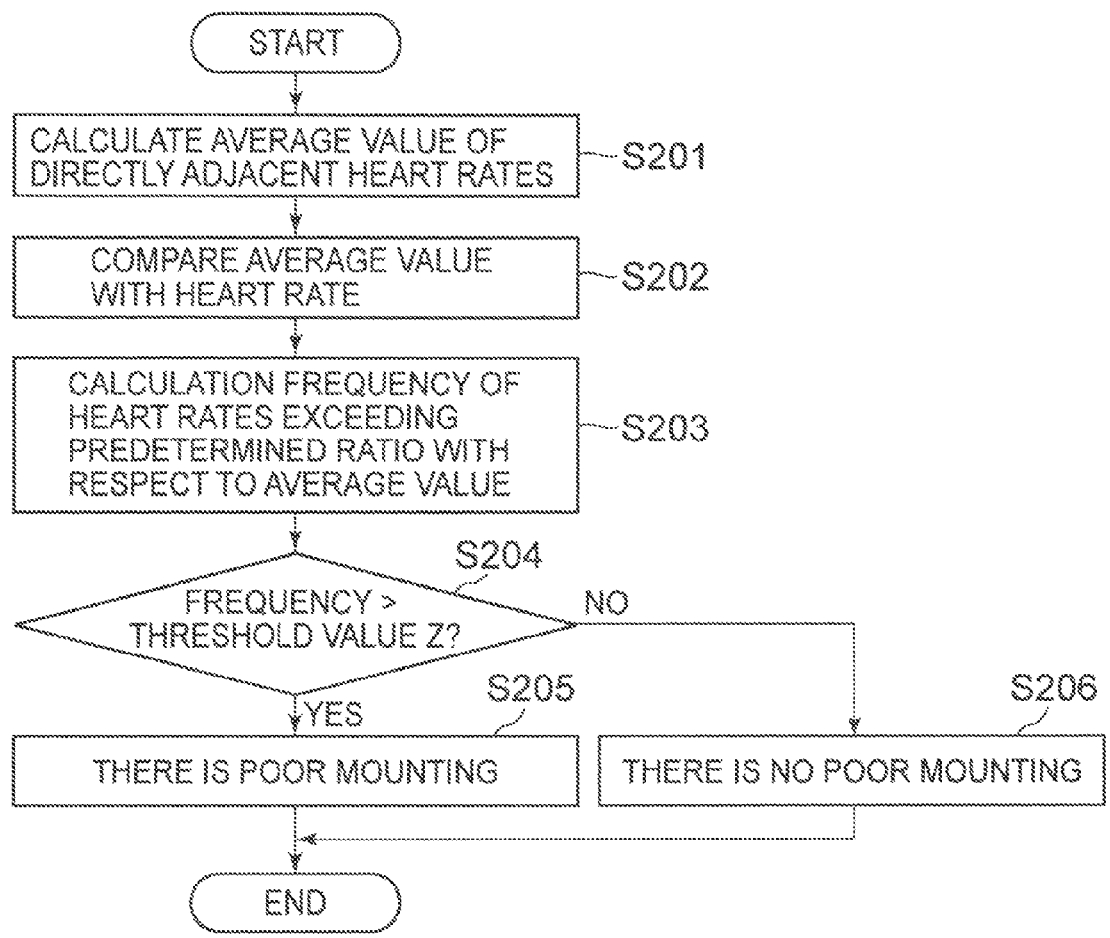
FIG. 14 is a flowchart illustrating an example of the process of detecting poor mounting according to the second embodiment of the present invention.

FIG. 14 is a flowchart illustrating an example of the process of detecting poor mounting according to the present embodiment. The process shown in the present figure corresponds to the above-described process in step S106 (refer to FIG. 13).

First, the poor mounting detection portion 2551 calculates an average value (movement average value) of a directly adjacent X heart rates with respect to the latest heart rate which has been calculated (step S201). Next, the poor mounting detection portion 2551 compares the calculated movement average value with the latest heart rate, determines whether or not the latest heart rate exceeds a predetermined ratio Y with respect to the calculated movement average value, and stores a determination result (step S202). In addition, the poor mounting detection portion 2551 calculates a frequency of heart rates exceeding the predetermined ratio Y with respect to the movement average value among directly adjacent $N_2$ heart rates on the basis of the determination result stored in step S202 (step S203).

Next, the poor mounting detection portion 2551 determines whether or not the calculated frequency is larger than a threshold value Z (a predetermined frequency Z) (step S204). If the calculated frequency is larger than the threshold value Z (step S204: YES), the poor mounting detection portion 2551 determines that there is poor mounting (step S205). On the other hand, if the calculated frequency is equal to or less than the threshold value Z (step S204: NO), the poor mounting detection portion 2551 determines that there is no poor mounting (step S206).

Figure 15:
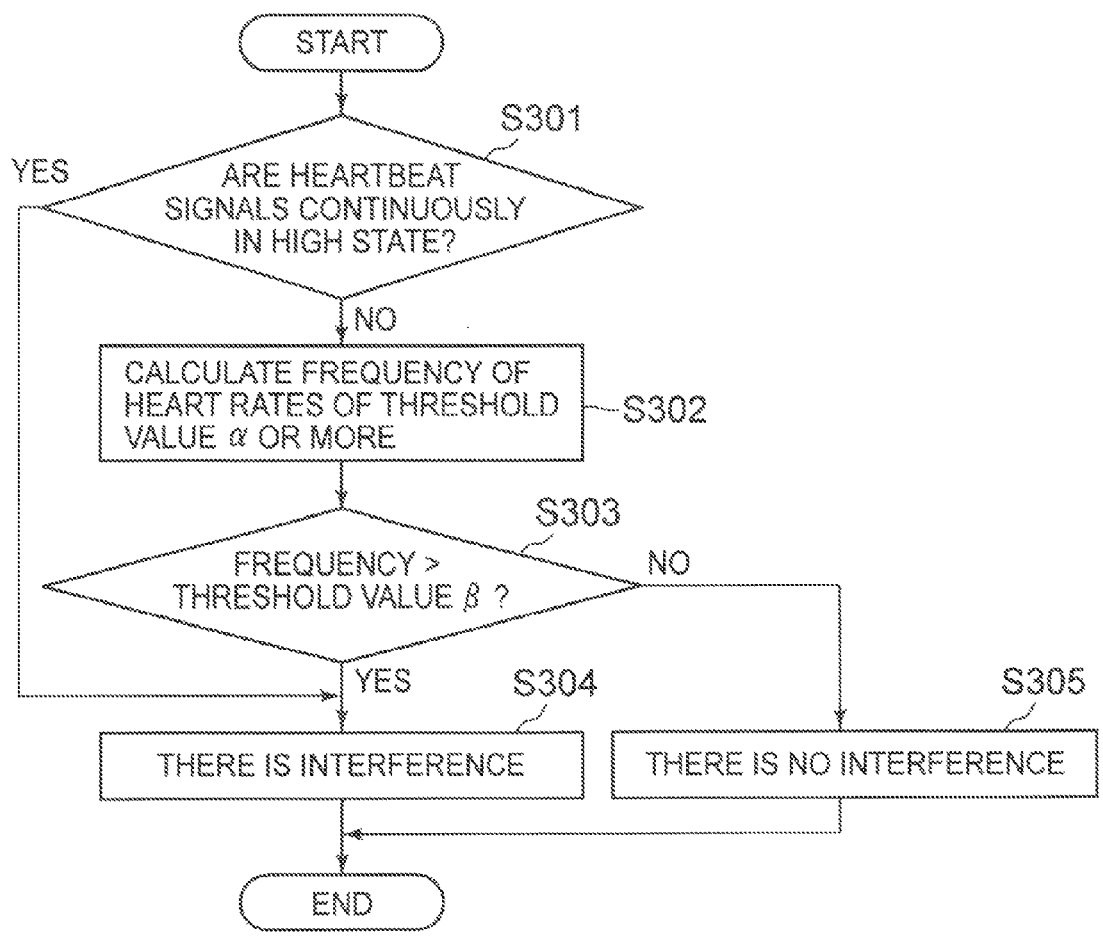
FIG. 15 is a flowchart illustrating an example of the process of detecting interference according to the second embodiment of the present invention.

FIG. 15 is a flowchart illustrating an example of the process of detecting interference according to the present embodiment. The process shown in the present figure corresponds to the above-described process in step S108 (refer to FIG. 13).

First, the interference detection portion 2552 determines whether or not heartbeat signals received by the reception circuit 280 via the antenna 290 are continuously in a high state for a predetermined time T or more (step S301). If the signals are continuously in a high state for the predetermined time T or more (step S301; YES), the interference detection portion 2552 determines that there is interference due to continuous external noise (step S304).

On the other hand, if the signals are not continuously in a high state for the predetermined time T or more (step S301: NO), the interference detection portion 2552 calculates a frequency of heart rates of a threshold value α or more among directly adjacent $N_2$ heart rates (step S302). Next, the interference detection portion 2552 determines whether or not the calculated frequency is larger than a threshold value β (predetermined frequency β) (step S303). If the calculated frequency is larger than the threshold value β (step S303: YES), the interference detection portion 2552 determines that there is interference due to isolated external noise (step S304). If the calculated frequency is equal to or less than the threshold value β (step S303: NO), the interference detection portion 2552 determines that there is no interference (step S305).

In addition, although, in the present embodiment, each parameter value for detecting noise is fixed, for example, each parameter value may be adjusted depending on a measurement state. Here, parameters for detecting poor mounting are the movement average number X when a movement average value is calculated, the ratio Y relative to a movement average value, the frequency Z, and the determination range $N_1$ for calculating a frequency. Further, parameters for detecting interference are the value α of a heart rate, the frequency β, and the determination range $N_2$ for calculating a frequency. For example, the poor mounting detection portion 2551 reduces the movement average number X when a heart rate is apt to vary, for example, when a measurement result is reset, before a measurement starts (before starting), or immediately after a measurement starts. When a measurement result is reset, before a measurement starts (before starting), or immediately after a measurement starts, since closeness between the heartbeat measuring device 100 and the user's skin is poor, and an electrocardiogram signal cannot be normally detected, a detected heart rate may be apt to vary. Alternatively, the poor mounting detection portion 2551 narrows the determination range $N_1$ by decreasing the frequency Z for detecting poor mounting, in a case where a heart rate is apt to vary. In addition, the interference detection portion 2552 narrows the determination range $N_2$ by decreasing the frequency β for detecting interference, in a case where a heart rate is apt to vary.

In addition, each parameter value may be adjusted depending on a noise amount. For example, the poor mounting detection portion 2551 may increase the movement average number X when a noise amount is large, and decrease the movement average number X when a noise amount is small. By increasing the movement average number X when a noise amount is large, it is possible to reduce influence of noise in a movement average value. Further, by decreasing the movement average number when a noise amount is small, it is possible to create a favorable response in hears rate display. Alternatively, the poor mounting detection portion 2551 may calculate a movement average value only using heart rates which are equal to or less than a predetermined value (for example, 300 (bpm)). Specifically, a movement average value may be calculated using directly adjacent $N_1$ heart rates which are equal to or less than a predetermined value (for example, 300 (bpm)). That is to say, the poor mounting detection portion 2551 does not use a heart rate which is larger than the predetermined value (for example, 300 (bpm)) for calculating a movement average value. Thereby, it is possible to calculate a movement average value from which influence of noise is reduced and to thereby detect poor mounting with nigh accuracy.

In addition, although, in the present embodiment, a measurement start command is input and then poor mounting and interference are detected, for example, if transfer to a measurement mode is performed, poor mounting or interference may be detected, and whether or not a heart rate can be measured may be displayed. Specifically, if transfer to a measurement mode is performed, the controller 250a makes the poor mounting detection portion 2551 detect poor mounting and the interference detection portion 2552 detect interference. In addition, the controller 250a displays information indicating that a measurement is possible on the display unit 240 in a case with neither poor mounting nor interference, and displays information indicating that a measurement is not possible on the display unit 240 in a case where there is poor mounting or interference. Thereby, a user can understand whether a measurement may be started.

In addition, although, in the present embodiment, when noise is detected, the controller 250a displays a mark indicating poor mounting or a mark indicating interference, the size of a mark may be varied depending on a noise amount. Specifically, in a case where it is determined that a noise amount is large, the controller 250a displays a large-sized mart of marks with large, middle, and small, sites, on the display unit 240. Further, in a case where it is determined that a noise amount is not large or small, the controller 250a displays a middle-sized mark on the display unit 240. Furthermore, if it is determined that a noise amount is small, the controller 250a displays a small-sized mark on the display unit 240. For example, the poor mounting detection portion 2551 determines that a noise amount is large in a case where a frequency of heart rates exceeding the predetermined ratio Y with respect to a movement average value is equal to or more than 30%. In addition, the poor mounting detection portion 2551 determines that a noise amount is not large or small in a case where a frequency of heart rates exceeding the predetermined ratio Y with respect to a movement average value is equal to or more than 20% and smaller than 30%. Further, the poor mounting detection portion 2551 determines that a noise amount is small in a case where a frequency of heart rates exceeding the predetermined ratio Y with respect to a movement average value is equal to or more than 5% and smaller than 20%. The interference detection portion 2552 determines that a noise amount is large in a case where a frequency of heart rates exceeding the predetermined value α is equal to or more than 30%, or in a case where continuous external noise is detected. In addition, the interference detection portion 2552 determines that a noise amount is not large or small in a case where a frequency of heart rates exceeding the predetermined value α is equal to or more than 20% and smaller than 30%. Further, the interference detection portion 2552 determines that a noise amount is small in a case where a frequency of heart rates exceeding the predetermined value α is equal to or more than 5% and smaller than 20%.

Figure 16A:
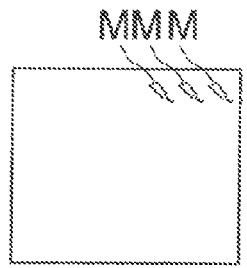
FIGS. 16A to 16C are diagrams illustrating an example where a mark is displayed depending on a noise amount according to the second embodiment of the present invention.
Figure 16B:
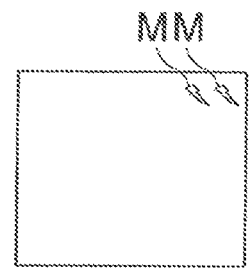
Figure 16C:
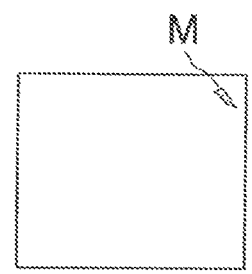

Alternatively, the controller 250a may vary the number of marks depending on a noise amount. FIGS. 16A to 16C are diagrams illustrating an example where a mark is displayed depending on a noise amount. For example, in a case where it is determined that a noise amount is large, the controller 250a displays three marks M indicating that there is noise on the display unit 240 (FIG. 16A). In addition, in a case where it is determined that a noise amount is not large or small, the controller 250a displays two marks M indicating that there is noise on the display unit 240 (FIG. 16B). Further, in a case where it is determined that a noise amount is small, the controller 250a displays a single mark indicating that there is noise on the display unit 240 (FIG. 16C).

As above, a user can understand whether a noise amount is large or small by varying mark display depending on a noise amount.

In addition, although, in the present embodiment, the controller 250a displays a mark when noise is detected, the present invention is not limited thereto, and a notification may be performed using other methods as long as a notification of abnormality can be performed. For example, when noise is detected, the controller 250a may display contents different from contents displayed on the display unit 240 in a normal state. Alternatively, when noise is detected, the controller 250a may display information indicating that noise is detected, using animation. Alternatively, when noise is detected, the controller 250a may display, on the display unit 240, fonts different from fonts which are displayed on the display unit 240 in a normal state.

In addition, although, in the present embodiment, the output device 200a calculates a heart rate on the basis of a heartbeat signal, the present invention is not limited thereto, and the heartbeat measuring device 100 may measure a heart rate on the basis of an electrocardiogram signal.

Further, although, in the present embodiment, abnormality is detected in order of the poor mounting determination (step S106) and the interference determination (step S108) in the measurement process shown in FIG. 13, the present invention is not limited thereto, and the poor mounting determination may be performed after performing the interference determination. Further, in a case where abnormality is detected through the first determination of the poor mounting determination or the interference determination, the next determination may be omitted.

As described above, according to the present embodiment, the output device 200a detects poor mounting of the heartbeat measuring device 100 or interference due to external noise on the basis of a received heartbeat signal, and performs a notification thereof. Thereby, since a user can understand poor mounting by the notification of the poor mounting, the user retightens the belt of the heartbeat measuring device 100 and wets the sensor unit (the electrode 121 and the electrode 122) of the heartbeat censuring device 100 so as to correctly mount the heartbeat measuring device 100, thereby removing noise. Further, since a user can understand interference by the notification of the interference, the user may become distant from peripheral people so as to remove external noise, and can understand that a heart rate is not correctly measured due to the surrounding environment.

In addition, a program for realizing the functions of the processing units of the present invention may be recorded on a computer readable recording medium, and the program recorded on the recording medium may be read to a computer system and be executed, thereby measuring a heart rate. Further, the "computer system" described here includes an OS or hardware such as peripheral devices. Furthermore, the "computer system" includes a WWW system provided with a home page providing circumstances for display circumstances). The "computer readable recording medium" refers to a portable medium such as a flexible disk, a magneto-optical disc, a ROM, or a CD-ROM, and a storage device such as a hard disk embedded in the computer system. Further, the "computer readable recording medium" includes a medium which holds a program for a specific time, such as a volatile memory (RAM) inside the computer system which is a server or a client when the program is transmitted via a network such as the Internet or a communication line such as a telephone line.

Further, the program may be transmitted to other computer systems from the computer system which stores the program in a storage device or the like, via a transmission medium, or a transmission wave in the transmission medium. Here, the "transmission medium" transmitting the program refers to a medium which has a function of transmitting information, like a network (communication network) such as the Internet, or a communication line such as a telephone line. In addition, the program may realize some of the above-described functions. Further, a so-called differential file (differential program) which can realize the above-described functions by a combination with a program which has already been recorded in a computer system may be used.

What is claimed is:

1. A heartbeat measuring device comprising:
    a measurement unit that measures a heart rate of a user;
    an information storage unit that stores unique information regarding a heart rate unique to the user or information regarding a detected heartbeat of the user, the unique information including at least one of an exercise frequency and an exercise event of the user;
    a determination unit that determines whether or not a heartbeat measurement state of the user is normal on the basis of the unique information or the information regarding a heartbeat stored in the information storage unit; and
    a threshold value calculation unit that calculates a threshold value of a heart rate for determining whether or not a heart rate of the user is a normal value on the basis of the unique information stored in the information storage unit and the heart rate measured by the measurement unit, the threshold value calculation unit being configured to perform a number of measurements for obtaining an average value of heart rates on the basis of at least one of the exercise frequency and the exercise event of the user, and being configured to calculate the threshold value on the basis of the unique information and the obtained average value of heart rates.

2. A heartbeat measuring device comprising:
    a measurement unit that measures a heart rate of a user by calculating a heart rate according to a pulse interval of an electrocardiogram signal from the user, comparing a first value which is the calculated heart rate and a second value which is an integral multiple of the heart rate with a previously measured heart rate among a plurality of heart rates measured by the measurement unit for each specific time, and outputting a value closer to the previously measured heart rate of the first value and the second value as the measured heart rate;

an information storage unit that stores unique information regarding a heart rate unique to the user or information regarding a detected heartbeat of the user;

a determination unit that determines whether or not a heartbeat measurement state of the user is normal on the basis of the unique information or the information regarding a heartbeat stored in the information storage unit; and a threshold value calculation unit that calculates a threshold value of a heart rate for determining whether or not a heart rate of the user is a normal value on the basis of the unique information stored in the information storage unit and the heart rate measured by the measurement unit.

3. A heartbeat measuring device comprising:

an information storage unit that stores unique information regarding a heart rate unique to a user or information regarding a detected heartbeat of the user, the unique information including at least one of a stable heart rate and a maximal heart rate of the user;

a determination unit that determines whether or not a heartbeat measurement state of the user is normal on the basis of the unique information or the information regarding a heartbeat stored in the information storage unit; and a threshold value calculation unit that calculates a threshold value of a heart rate for determining whether or not a heart rate of the user is a normal value on the basis of the unique information stored in the information storage unit;

wherein the threshold value calculation unit calculates an upper limit threshold value of a heart rate which is a normal value on the basis of the maximal heart rate when the maximal heart rate is included in the unique information, and calculates a lower limit threshold value of the heart rate which is a normal value on the basis of the stable heart rate when the stable heart rate is included in the unique information.

4. The heartbeat measuring device according to claim 3, further comprising a measurement unit that measures a heart rate of the user; wherein the threshold value calculation unit calculates the threshold value on the basis of the unique information and the heart rate measured by the measurement unit; and wherein the determination unit compares the heart rate measured by the measurement unit with the threshold value calculated by the threshold value calculation unit and determines whether or not the heart rate is a normal value.

5. The heartbeat measuring device according to claim 4, further comprising: a notification unit that performs a notification when it is determined by the determination unit that the heart rate is not a normal value.

6. The heartbeat measuring device according to claim 5, wherein the notification unit performs a notification when a heart rate measured after a specific time period has elapsed from starting measurement of a heart rate of the user by the measurement unit is determined as not being a normal value by the determination unit.

7. The heartbeat measuring device according to claim 3, further comprising:

an input unit that receives an input of the unique information and stores the input unique information in the information storage unit; and a measurement unit that measures a heart rate of the user;

wherein the threshold value calculation unit calculates the threshold value on the basis of the unique information and the heart rate measured by the measurement unit.

8. The heartbeat measuring device according to claim 3, further comprising:

a mounting unit for mounting the heartbeat measuring device on the arm of the user; and a measurement unit that measures a heart rate of the user;

wherein the threshold value calculation unit calculates the threshold value on the basis of the unique information and the heart rate measured by the measurement unit.

9. A heartbeat measuring device comprising:

a measurement unit that measures a heart rate of a user;

an information storage unit that stores unique information regarding a heart rate unique to the user or information regarding a detected heartbeat of the user;

a determination unit that determines whether or not a heartbeat measurement state of the user is normal on the basis of the unique information or the information regarding a heartbeat stored in the information storage unit;

an abnormality detection unit that detects an abnormality corresponding to poor mounting of the heartbeat measuring device or interference due to external noise on the basis of a heart rate measured by the measurement unit; and a notification unit that performs a notification when the abnormality is detected by the abnormality detection unit;

wherein the notification unit changes information to be notified on the basis of a detection result by the abnormality detection unit.

10. The heartbeat measuring device according to claim 9, wherein the abnormality detection unit detects poor mounting of the heartbeat measuring device on the basis of a plurality of heart rates measured by the measurement unit.

11. The heartbeat measuring device according to claim 9, further comprising:

a communication unit that receives a signal indicating a heartbeat using wireless communication;

wherein the abnormality detection unit detects interference due to external noise on the basis of a plurality of signals received by the communication unit.

12. The heartbeat measuring device according to claim 9, wherein the abnormality detection unit detects interference due to external noise when heart rates of a predefined value or more are measured to be more than a predetermined frequency.

13. The heartbeat measuring device according to claim 9, wherein the abnormality detection unit detects interference due to continuous external noise when continuous signals are received by the communication unit for a predefined time or more.

14. A heartbeat measuring device comprising:

an information storage unit that stores unique information regarding a heart rate unique to a user or information regarding a detected heartbeat of the user;

a determination unit that determines whether or not a heartbeat measurement state of the user is normal on the basis of the unique information or the information regarding a heartbeat stored in the information storage unit;

an abnormality detection unit that detects abnormality from a heart rate measured by the measurement unit which measures the heart rate of the user; and a notification unit that performs a notification when abnormality is detected by the abnormality detection unit;

wherein the abnormality detection unit detects poor mounting of the heartbeat measuring device on the basis of a plurality of heart rates measured by the measurement unit; and wherein the abnormality detection unit determines poor mounting of the heartbeat measuring device when a predetermined frequency of signals exceeding a predetermined ratio or value with respect to an average value during a predetermined latest time period is detected.

* * * * *